United States Patent [19]
Kiel

[11] Patent Number: 6,077,974
[45] Date of Patent: Jun. 20, 2000

[54] PROCESS FOR THE CONTINUOUS PREPARATION OF AMINO-HALO-GENOPHENYL ALKYL THIOETHERS

[75] Inventor: Wolfgang Kiel, Odenthal, Germany

[73] Assignee: Bayer Aktiengesellschaft, Leverkusen, Germany

[21] Appl. No.: 09/358,275

[22] Filed: Jul. 21, 1999

[30] Foreign Application Priority Data

Jan. 29, 1998 [DE] Germany .................... 198 34 102

[51] Int. Cl.[7] ................................ C07C 209/00
[52] U.S. Cl. ........................... 564/422; 564/417
[58] Field of Search .............................. 564/422

[56] References Cited

FOREIGN PATENT DOCUMENTS 0775693   5/1977   European Pat. Off. .
0 306 222  3/1989  European Pat. Off. .

OTHER PUBLICATIONS

Chem. Ind. 53, pp. 103–109, (month unavailable) 1994, Catalysis of Oranic Reactions edited by John R. Kosak, High Selectivities in Hydrogenation of Halogenonitrobenzenes on Pd, Pt, or Raney Nickel as Catalysts, Georges Cordier.

Primary Examiner—Paul J. Killos
Attorney, Agent, or Firm—Joseph C. Gil; Diderico van Eyl

[57] ABSTRACT

Amino-halogenophenyl alkyl thioethers prepared in an advantageous manner by catalytic reduction of the corresponding nitro compound by the nitro compound being continuously hydrogenated with hydrogen in the presence of a supported noble-metal catalyst.

11 Claims, No Drawings

PROCESS FOR THE CONTINUOUS PREPARATION OF AMINO-HALO-GENOPHENYL ALKYL THIOETHERS

FIELD OF THE INVENTION

The present invention relates to a continuous process for the preparation of aminohalogenophenyl alkyl thioethers by selective catalytic hydrogenation of the corresponding nitro compounds.

BACKGROUND OF THE INVENTION

Amino-halogenophenyl alkyl thioethers are intermediates for the preparation of crop protection compositions (see, e.g., EP-A 306,222).

Under the conditions of a catalytic hydrogenation, it is expected that the feed materials undergo elimination of halogen atoms and alkylmercapto groups (see, e.g., Chem. Ind. 53, 103–109 (1994) and Comparative Example 1).

A discontinuous process for the preparation of 2-amino-6-chlorophenyl alkyl thioethers by catalytic hydrogenation using a Raney nickel catalyst is known (see DE-A 1,943,475). The selectivity which is achieved with this discontinuous process does, however, deteriorate significantly when attempts are made to carry it out continuously (see Comparative Example 1). The increasing elimination of chlorine and alkylmercapto groups also leads to a premature loss in activity of the Raney nickel catalyst, meaning that in a continuous process it has to be replaced more frequently, which would require additional expenditure.

We have now found a process for the preparation of amino-halogenophenyl alkyl thioethers by catalytic reduction of the corresponding nitro compounds which is characterized in that the nitro compound is continuously hydrogenated with hydrogen in the presence of a supported noble-metal catalyst.

SUMMARY OF THE INVENTION

The invention relates to a process for preparing amino-halogenophenyl alkyl thioethers by catalytic reduction of corresponding nitro compounds, characterized in that the nitro compound is continuously hydrogenated with hydrogen in the presence of a supported noble-metal catalyst.

DESCRIPTION OF THE INVENTION

In the novel process, nitro compounds such as the compounds according to formula (I) can be used:

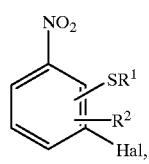

(I)

where
SR$^1$ is in the ortho- or para-position relative to the nitro group and
R$^1$ is C$_1$–C$_{18}$-alkyl, C$_3$–C$_8$-cycloalkyl or C$_7$–C$_{10}$-arylalkyl groups,
R$^2$ is hydrogen, C$_1$–C$_4$-alkyl, C$_1$–C$_4$-alkoxy or benzyl groups, and
Hal is chlorine or bromine groups.

The corresponding amino-halogenophenyl alkyl thioethers of the formula (II) can be obtained from such nitro compounds

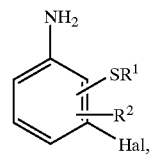

(II)

where
SR$^1$ is in the ortho- or para-position relative to the amino group, and
R$^1$, R$^2$ and Hal are as defined for formula (I).

In the formulae (I) and (II), R$^2$ is preferably in the ortho-position relative to Hal.

Examples of C$_1$–C$_4$-alkyl include methyl, ethyl, n-propyl, i-propyl, n-butyl, i-butyl and tert-butyl. Examples of C$_1$–C$_{18}$-alkyl include additionally the isomeric amyls, hexyls, octyls, decyls, dodecyls, heptadecyls and octadecyls. Examples of C$_3$–C$_8$-cycloalkyl include cyclopropyl, cyclobutyl, cyclopentyl, cyclohexyl, cycloheptyl, methylcyclopropyl, dimethylcyclopropyl, methylcyclopentyl, dimethylcyclopentyl, methylcyclohexyl and dimethylcyclohexyl. Examples of C$_7$–C$_{10}$-arylalkyl groups include benzyl, α- and β-phenylethyl, phenylpropyl and phenylbutyl. Examples of C$_1$–C$_4$-alkoxy groups include methoxy, ethoxy, propoxy, n-butoxy and i-butoxy groups.

Preferred alkyl groups include methyl, ethyl and isopropyl, preferred cycloalkyl groups include cyclopropyl, cyclopentyl and cyclohexyl and the corresponding methyl- and dimethylcycloalkyls, preferred arylalkyl groups include benzyl and phenylethyl, and preferred alkoxy groups include methoxy and ethoxy.

R$^1$ is preferably one of the alkyl groups listed as being preferred, and R$^2$ is preferably hydrogen or one of the alkyl groups listed as being preferred.

Particularly preferred nitro compounds of the formula (I) include 2-chloro-6-nitrophenyl methyl thioether, 2-chloro-6-nitrophenyl isopropyl thioether, 2-fluoro-6-nitrophenyl isopropyl thioether, 4-chloro-6-nitrophenyl isopropyl thioether, 4-fluoro-6-nitrophenyl isopropyl thioether, 2-chloro-4-nitrophenyl isopropyl thioether and 2-fluoro-4-nitrophenyl isopropyl thioether, from which the corresponding amino compounds of the formula (II) are obtained.

The novel process is generally carried out in the presence of a solvent. Suitable examples include alcohols, alkanes, cycloalkanes and aromatics. Preference is given to methanol, ethanol, isopropanol, methylcyclohexane and toluene. It is also possible to use any mixtures of said solvents. The nitro compound used and the amino compound obtained do not necessarily have to be completely soluble in the respective solvent. It suffices for some of it to be dissolved and the remainder to be present in suspended form. Preference is given to using methanol, ethanol, isopropanol, methylcyclohexane and/or toluene in amounts such that the nitro compounds used and the amino compounds obtained can be present in completely dissolved form.

It is an essential feature of the present invention for the continuous preparation of amino-halogenophenyl alkyl thioethers that a supported noble-metal catalyst is used. The noble metals can, for example, be palladium or platinum, and the support materials can, for example, be aluminium oxides, silicas or various charcoals (for example wood charcoal, animal charcoal or activated charcoal). Preference is given to platinum-on-charcoal catalysts. The supported catalysts can comprise, for example, from 0.1 to 10% by weight, preferably from 1 to 8% by weight, of noble metal.

It is further preferable to use the supported noble-metal catalysts, in particular platinum-on-charcoal catalysts, in sulphidized form. The amino-halogenophenyl alkyl thioethers are then frequently produced in even better selectivities. Sulphidized supported noble-metal catalysts can comprise, for example, from 0.001 to 1% by weight of sulphur (based on the noble metal). This amount is preferably from 0.005 to 0.5% by weight.

Catalysts which are suitable for the novel process, including those in sulphidized form, are available commercially.

The amount of catalyst, based on the nitro compounds used, can be varied within wide limits. For example, based on a throughput of nitro compound of 1 mol per hour, from 3 to 30 g of catalyst (total of noble metal+support) can be present in the reaction vessel. This amount is preferably from 5 to 15 g of catalyst.

The novel process can be carried out, for example, at temperatures in the range from 20 to 150° C. and, for example, pressures in the range from atmospheric pressure to 300 bar. Preference is given to ranges from 30 to 120° C. and from 10 to 150 bar.

The novel process can, for example, be implemented using reactors with residence times of, for example, from 10 to 400 minutes. The residence time is preferably from 30 to 180 minutes. Suitable reactor types include, for example, stirred autoclaves, loop reactors and tubular reactors.

The prepared amino-halogenophenyl alkyl thioethers can be separated off and isolated using various methods. For example, a fully reacted reaction mixture can be removed from the reactor in an amount corresponding to the feed. The catalyst (e.g., by filtration) and the solvent (e.g., by distillation) can be removed from the reaction mixture drawn off and be recycled. It is also possible for the reactor to be provided with equipment which prevents catalyst discharge and removes and works up only liquid constituents of the fully reacted reaction mixture. From mixtures which essentially comprise solvent and prepared product, it is possible to crystallize the prepared product, where necessary also by cooling, and then to remove it, e.g., by filtration. Other work-up and isolation methods are also conceivable.

It is advantageous to remove some or all of the catalyst from time to time such as when its activity has diminished, e.g., after an operating time of from 2 to 10 days, and be replaced with fresh catalyst. The prepared amino-halogenophenyl alkyl thioethers are generally already in a purity of 99% or above, depending on their separation and isolation.

The novel process has the advantage that it can be used to prepare amino-halogenophenyl alkyl thioethers continuously in high purities and with low by-product formation (e.g., caused by elimination of chlorine and/or alkylthio groups). This is particularly surprising since noble metals are generally more sensitive to sulphur compounds than Raney nickel. Sulphur compounds frequently deactivate noble-metal catalysts. Here, however, the opposite effect occurs.

The invention is further described in the following illustrative examples. All references to parts and percentages are based on weight unless otherwise indicated.

EXAMPLES

Example 1

80 g of 2-chloro-6-nitrophenyl isopropyl thioether, 320 g of methanol and 9.6 g of catalyst (platinum on charcoal, 5% by weight) were introduced into a 0.7 l autoclave. After the autoclave had been flushed with nitrogen, hydrogen was injected to a pressure of 50 bar and the autoclave was heated to 80° C. After hydrogenation had started, the hydrogen pressure was increased to 80 bar and maintained at 80 bar. A mixture of the above composition was then continuously pumped in into the fully reacted reaction mixture, and the same amount of fully reacted reaction mixture was continuously removed. The catalyst was separated off from the removed reaction mixture by filtration, and methanol was separated off therefrom by distillation and both were returned to the reaction.

For a residence time in the reactor of 30 minutes, this method produced 2-amino-6-chlorophenyl isopropyl thioether with a purity of 99.28% (GC). Chlorine-free aromatics were formed only in an amount less than 0.1%, and aromatics free from isopropylmercapto groups were likewise only formed in an amount less than 0.1%.

Example 2

The procedure of Example 1 was repeated, but using 9.6 g of a sulphidized catalyst from Engelhard which contained 3% by weight of platinum on charcoal.

For a residence time in the reactor of 20 minutes, this method produced 2-amino-6-chlorophenyl isopropyl thioether with a purity of 99.61% (GC). Chlorine-free aromatics and aromatics free from isopropylmercapto groups were in each case only formed in amounts less than 0.1%.

Comparative Example 1

Example 1 was repeated, but using, as catalyst, 6 g of Raney nickel of the type Ra Ni37S (Bayer).

For a residence time in the reactor of 60 minutes, this method produced 2-amino-6-chlorophenyl isopropyl thioether with a purity of 97.33% (GC). Chlorine-free aromatics were formed in an amount of 2.1%, and aromatics free from isopropylmercapto groups were formed in an amount of 0.52%.

Although the invention has been described in detail in the foregoing for the purpose of illustration, it is to be understood that such detail is solely for that purpose and that variations can be made therein by those skilled in the art without departing from the spirit and scope of the invention.

What is claimed is:

1. A process for preparing an amino-halogenophenyl alkyl thioether comprising catalytically reducing a corresponding nitro compound in a reaction vessel, wherein the nitro compound is continuously hydrogenated with hydrogen in the presence of a catalyst component comprising a supported noble-metal catalyst.

2. The process of claim 1, wherein the nitro compound used comprises a compound having the formula (I)

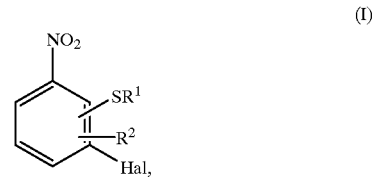

wherein
   $SR^1$ is in the ortho- or para-position relative to the nitro group;
   $R^1$ comprises a group selected from the group consisting of $C_1$–$C_{18}$-alkyl groups, $C_3$–$C_8$-cycloalkyl groups and $C_7$–$C_{10}$-arylalkyl groups;

R² comprises a component selected from the group consisting of hydrogen atoms, $C_1$–$C_4$-alkyl groups, $C_1$–$C_4$-alkoxy groups and benzyl groups; and Hal comprises a halogen component selected from the group consisting of chlorine and bromine;

and amino-halogenophenyl alkyl thioethers of the formula (II) are obtained

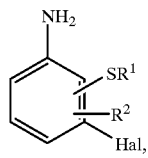

(II)

wherein

SR¹ is in the ortho- or para-position relative to the amino group, and

R¹, R² and Hal are as defined for formula (I).

3. The process of claim 1, wherein the nitro compound of formula (I) is selected from the group consisting of 2-chloro-6-nitrophenyl methyl thioether, 2-chloro-6-nitrophenyl isopropyl thioether, 2-fluoro-6-nitrophenyl isopropyl thioether, 4-chloro-6-nitrophenyl isopropyl thioether, 4-fluoro-6-nitrophenyl isopropyl thioether, 2-chloro-4-nitrophenyl isopropyl thioether and 2-fluoro-4-nitrophenyl isopropyl thioether and the corresponding amino compounds of formula (II) are prepared.

4. The process of claim 1, wherein the process is carried out in the presence of a solvent component selected from the group consisting of alcohols, alkanes, cycloalkanes and aromatics.

5. The process of claim 1, wherein the catalyst component comprises a component selected from the group consisting of palladium and platinum-on-charcoal catalysts.

6. The process of claim 1, wherein the catalyst component comprises sulphidized supported noble-metal catalysts.

7. The process of claim 1, wherein based on a throughput of the nitro compound of 1 mol/h, and from about 3 to about 30 g of the catalyst component are present in the reaction vessel.

8. The process of claim 1, wherein the process is carried out at a temperature ranging from about 20 to about 150° C. and at a pressure ranging from about atmospheric pressure to about 300 bar.

9. The process of claim 1, wherein the process is carried out in a reactor having a residence time ranging from about 10 to about 400 minutes.

10. The process of claim 1, wherein a fully reacted reaction mixture is removed from the reactor in an amount corresponding to the feed, and the catalyst component and solvent are removed therefrom and recycled.

11. The process of claim 1, wherein the amino-halogenophenyl alkyl thioether is produced with a purity of at least about 99%.

* * * * *